United States Patent
Oberdoerfer et al.

(10) Patent No.: US 9,157,895 B2
(45) Date of Patent: Oct. 13, 2015

(54) SYSTEMS AND METHODS FOR VIEWING DATA GENERATED BY ROTATIONAL SCANNING IN NON-DESTRUCTIVE TESTING

(71) Applicant: General Electric Company, Schenectady, NY (US)

(72) Inventors: York Oberdoerfer, Langenfeld (DE); Weiwei Zhang, Cologne (DE)

(73) Assignee: GENERAL ELECTRIC COMPANY, Schenectady, NY (US)

(*) Notice: Subject to any disclaimer, the term of this patent is extended or adjusted under 35 U.S.C. 154(b) by 339 days.

(21) Appl. No.: 13/628,066

(22) Filed: Sep. 27, 2012

(65) Prior Publication Data
US 2014/0083192 A1    Mar. 27, 2014

(51) Int. Cl.
G01N 29/265 (2006.01)
G01N 29/06 (2006.01)
G01N 29/22 (2006.01)
G01S 7/52 (2006.01)
G01S 15/89 (2006.01)

(52) U.S. Cl.
CPC .......... *G01N 29/0645* (2013.01); *G01N 29/069* (2013.01); *G01N 29/226* (2013.01); *G01S 7/52061* (2013.01); *G01S 7/52063* (2013.01); *G01S 15/894* (2013.01); *G01S 15/8925* (2013.01)

(58) Field of Classification Search
CPC ............ G01S 7/52061; G01S 15/8925; G01S 15/894; G01S 7/52063; G01N 29/0645; G01N 29/226; G01N 29/069
USPC ............................. 73/627, 602, 606, 625, 618
See application file for complete search history.

(56) References Cited

U.S. PATENT DOCUMENTS

| | | | |
|---|---|---|---|
| 4,324,140 A | | 4/1982 | Auld |
| 4,470,122 A | * | 9/1984 | Sarr ............................. 702/150 |
| 5,546,807 A | * | 8/1996 | Oxaal et al. ..................... 73/606 |
| 6,491,634 B1 | * | 12/2002 | Leavitt et al. ................. 600/447 |
| 6,540,682 B1 | * | 4/2003 | Leavitt et al. ................. 600/447 |
| 6,645,148 B2 | * | 11/2003 | Nguyen-Dinh et al. ...... 600/459 |
| 6,746,402 B2 | * | 6/2004 | Ustuner ........................ 600/462 |
| 7,283,654 B2 | * | 10/2007 | McLain ........................ 382/128 |
| 8,717,843 B2 | * | 5/2014 | Cerofolini .......................... 367/7 |
| 2003/0089171 A1 | | 5/2003 | Kenefick et al. |
| 2003/0101820 A1 | | 6/2003 | Siong |
| 2006/0052697 A1 | | 3/2006 | Hossack et al. |
| 2007/0068907 A1 | | 3/2007 | Batzinger et al. |
| 2009/0279772 A1 | | 11/2009 | Sun et al. |
| 2009/0283569 A1 | | 11/2009 | Ramaswamy et al. |
| 2010/0220910 A1 | | 9/2010 | Kaucic et al. |

(Continued)

FOREIGN PATENT DOCUMENTS

CN    101726540 A    6/2010

OTHER PUBLICATIONS

Search Report from PCT/US2013/056602 dated Dec. 2, 2013.

(Continued)

*Primary Examiner* — J M Saint Surin
(74) *Attorney, Agent, or Firm* — Cooper Legal Group, LLC

(57) ABSTRACT

The present application relates to a non-destructive testing system. The non-destructive testing system may include an ultrasonic probe and a hand-held display in communication with the ultrasonic probe. The hand-held display may be configured to display C-scan images or S-scan images.

20 Claims, 3 Drawing Sheets

(56) References Cited

U.S. PATENT DOCUMENTS

| | | |
|---|---|---|
| 2011/0182495 A1 | 7/2011 | Sun et al. |
| 2011/0222754 A1 | 9/2011 | Zhao et al. |
| 2011/0239768 A1 | 10/2011 | Berke et al. |
| 2011/0247417 A1 | 10/2011 | Oberdoerfer et al. |
| 2012/0024067 A1 | 2/2012 | Oberdoerfer et al. |
| 2012/0134233 A1 | 5/2012 | Lin et al. |
| 1352/8862000 | 6/2012 | Oberdoerfer |

OTHER PUBLICATIONS

Berke M, et al: "Phased array technology for standard ultrasonic testing", Insight (Non-Destructive Testing and Condition Monitoring), British Institute of Non-Destr. Test., Northampton, GB, vol. 48, No. 4, Apr. 1, 2006.

* cited by examiner

SYSTEMS AND METHODS FOR VIEWING DATA GENERATED BY ROTATIONAL SCANNING IN NON-DESTRUCTIVE TESTING

TECHNICAL FIELD

The present disclosure relates generally to ultrasonic probes used for non-destructive testing and more particularly relates to systems and methods for viewing data generated by rotational scanning in non-destructive testing with reduced storage and computational requirements.

BACKGROUND OF THE INVENTION

Non-destructive testing such as ultrasonic testing and the like may be used to inspect various types of materials and components. Specifically, ultrasonic testing is a suitable method for finding internal anomalies and/or certain types of material characteristics in most types of sound conducting materials. Such sound conducting materials include most metals and other types of substantially rigid materials. Generally described, an ultrasonic probe detects anomalies or other characteristics upon changes in the reflection of sound waves on a boundary surface of the component or the anomaly. Ultrasonic testing has the advantage of detecting such internal characteristics with a generally high degree of accuracy.

Data generated by ultrasonic testing may be presented in a number of different formats. For example, the scan data may be presented as an A-scan (energy received as a function of time), a B-scan (cross-sectional view), a C-scan (plan view), an S-scan (sectional view), and the like. A one-dimensional or two-dimensional ultrasonic probe may generate the scans. A number of the individual scans may be combined so as to generate three-dimensional views.

As opposed to similar types of ultrasonic devices used in the healthcare field, non-destructive testing tools used in, for example, the oil and gas industry and the like, may be relatively small, handheld, and battery driven. Moreover, such non-destructive testing tools generally need to last in the field for at least a complete shift (about 8 hours or more) without recharging. Generating three-dimensional views, however, requires significant memory and computational power.

There is, thus, a desire for improved systems and methods of non-destructive testing such as ultrasonic testing and the like. Such improved systems and methods may present ultrasonic and other types of non-destructive testing data in a useful and efficient fashion while requiring less computational resources.

SUMMARY OF THE INVENTION

The present application relates to a non-destructive testing system. The non-destructive testing system may include an ultrasonic probe and a hand-held display in communication with the ultrasonic probe. The hand-held display may be configured to display C-scan images or corresponding S-scan images.

The present application further describes a method of viewing non-destructive test data. The method may include the steps of maneuvering an ultrasonic probe about a work piece, ultrasonically scanning the work piece, displaying a number of C-scan images, selecting one of the of C-scan images, and displaying a S-scan image corresponding to the selected C-scan image.

The present application further describes a non-destructive testing system. The non-destructive testing system may include a two-dimensional array ultrasonic probe and a hand-held display in communication with the ultrasonic probe. The hand-held display may be configured to display a number of C-scan images in a radar-like view or a corresponding S-scan image.

These and other features and improvements of the present application will become apparent to one of ordinary skill in the art upon review of the following detailed description when taken in conjunction with the several drawings and the appended claims.

DETAILED DESCRIPTION

Figure 1:
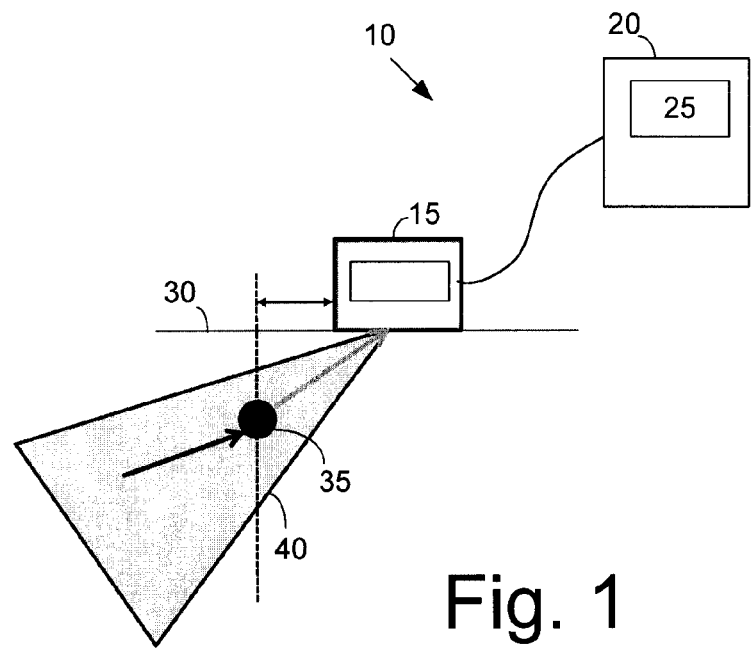
FIG. 1 is a schematic diagram of a known non-destructive testing system with an ultrasonic probe.

Referring to the drawings, in which like numerals refer to like elements throughout the several views, FIG. 1 is a schematic diagram of a non-destructive testing system 10. The non-destructive testing system 10 includes an ultrasonic probe 15. Generally described, the ultrasonic probe 15 may be of conventional design and includes one or more arrays of transducers, a transmit beamformer, and a receive beamformer. The ultrasonic transducers may be arranged as a phase array. The transmit beamformer supplies electrical signals to the transducer arrays and the transducer arrays produce ultrasonic signals. The structure facing the transducer arrays scatters the ultrasonic energy back to the transducer arrays so as to generate received electric signals. Many different types of array processing techniques may be used for processing the received signals. The ultrasonic probe 15 is in communication with a control unit 20. The control unit 20 may include a display 25. Many different types of control units 20 and display 25 may be used.

The non-destructive testing system 10 typically may be used to test a work piece 30. The work piece 30 may have one or more anomalies 35 therein. The ultrasonic probe 15 may be configured to produce a number of S-scans 40 (sectional scans). In the S-scans 40, a first axis may represent the distance from an insonification location or a depth in the work piece 30 and a second axis may represent an azimuth or an insonification angle. Other types of scans such as a C-scan (plan view) and the like also may be generated and displayed on the display 25. A number of the S-scans 40 may be combined so as to produce a largely three-dimensional image. As described above, however, displaying such three-dimensional data may be complicated and may require significant amounts of memory and computational power.

Figure 2:
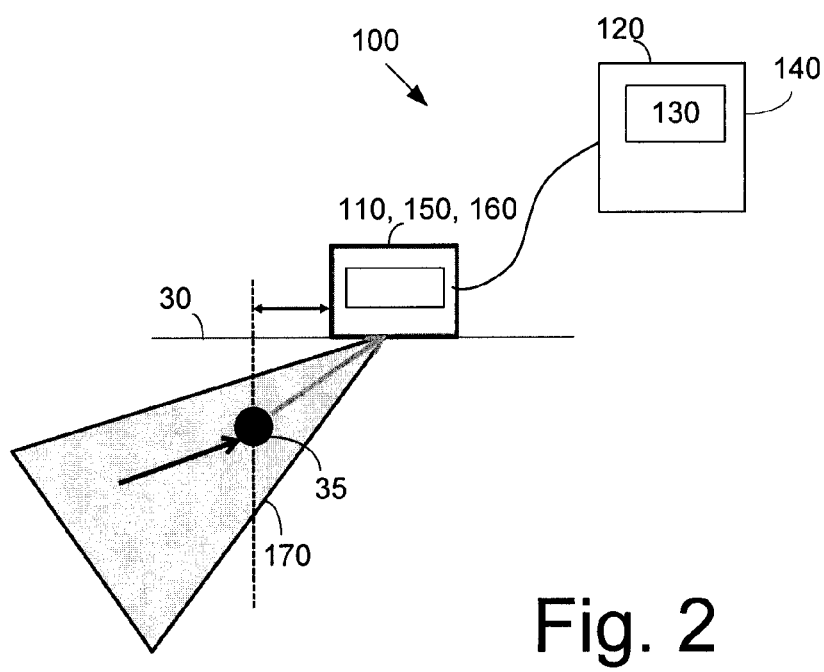
FIG. 2 is a schematic diagram of a non-destructive testing system with an ultrasonic probe as may be described herein.

FIG. 2 is a schematic diagram of a non-destructive testing system 100 as is described herein. Similar to that described above, the non-destructive testing system 100 includes an ultrasonic probe 110. The ultrasonic probe 110 may be of conventional design. The ultrasound probe 110 may be in communication with a control unit 120 and a display 130. In this example, the control unit 120 may be a handheld device 140. The handheld device 140 may be any type of portable equipment. The handheld device 140 also may be battery operated. The ultrasonic probe 110 may be a phased array device 150. Other components and other configurations may be used herein.

The ultrasonic probe 110 may be configured as a translational device 160. Specifically, the ultrasonic probe 110 may include a matrix of transducers arranged as a two-dimensional probe. The probe 110 thus may have discrete element separation in two directions such that a sound beam 170 may be controlled in a three-dimensional volume. Specifically, the beam 170 is rotated about a middle axis, perpendicular to a horizontal plane. The ultrasonic probe 110 thus may rotate the beam 170 about 360 degrees. Resolution in terms of data capture may be at each one degree step for a 360 degree scan or at any desired resolution. The resolution also may be varied for a particular type of application and/or type of work piece 30.

Figure 3:
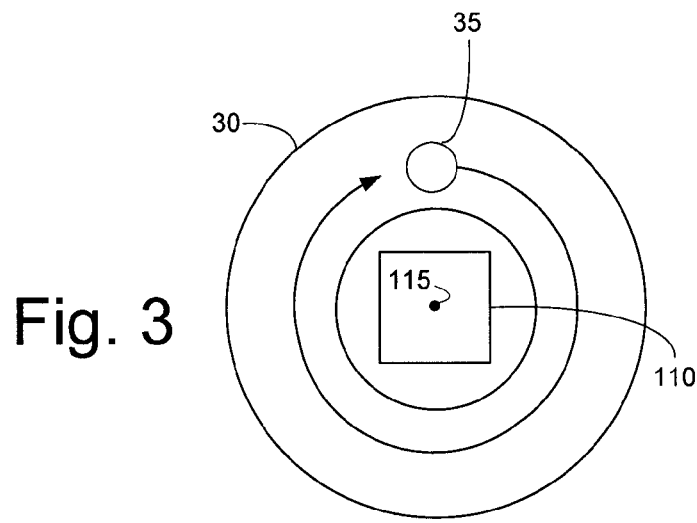
FIG. 3 is a plan view of the ultrasonic probe of the non-destructive testing system of FIG. 2 positioned within a work piece.

FIG. 3 shows the use of the non-destructive testing system 100 within the work piece 30 with the anomaly 35. The ultrasonic probe 110 may be positioned about the work piece 30 in the form of a tube. The ultrasonic probe 110 thus may rotate the beam 170 with a rotational axis 115 through the middle of the probe 110 and so as to produce any number of finely pitched scans. Other components and other configurations also may be used herein.

Figure 4:
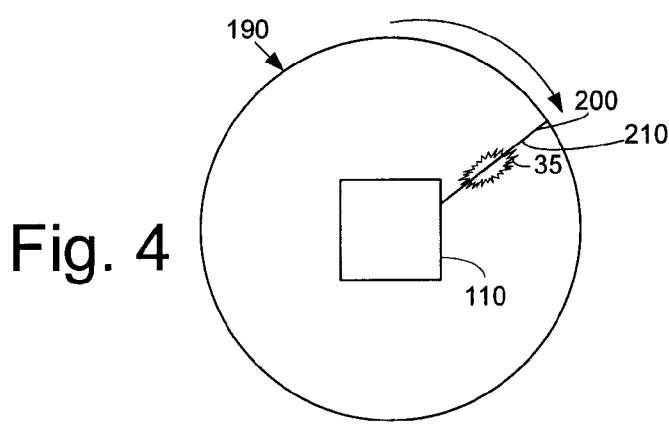
FIG. 4 is an example of a C-scan image produced by the non-destructive testing system of FIG. 2.
Figure 5:
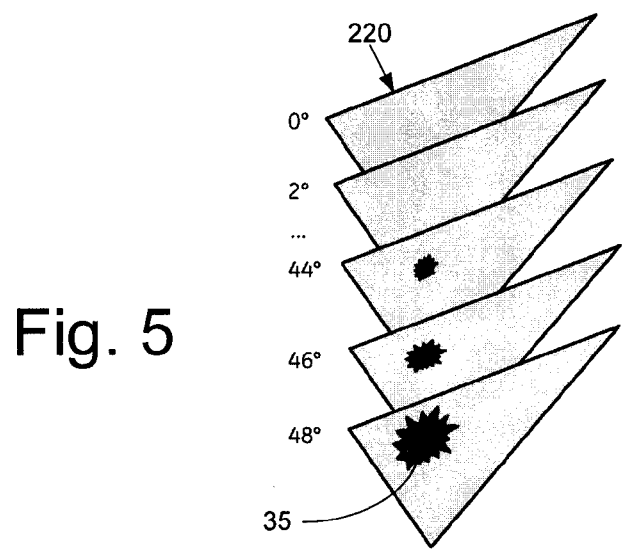
FIG. 5 is an example of a number of S-scan images produced by the non-destructive testing system of FIG. 2.

The ultrasonic probe 110 may produce a number of different scans. FIGS. 4 and 5 show examples of different types of scans produced and displayed by the display 130 of the non-destructive system 100. The ultrasonic probe 110 may produce both a number of C-scan images for top/down views and a number of S-scan images for side view imaging. FIG. 4 shows a number C-scan images 190 combined with a beam cursor 200 so as to provide a radar-like view 210.

FIG. 5 shows a number of S-scan images 220. Each S-scan image 220 may relate to an angle of interest along the 360 degrees of rotation based upon a position of the beam cursor 200 in the radar-like view 210 of the C-scan images 190. The user thus may toggle back and forth between the C-Scan images 190 and the associated S-scan images 220. Although a 360 degree scan is shown in FIG. 4, any smaller angle may be shown. If so, the resultant image would be similar to a pie slice as opposed to the entire pie shown herein. Other types of scans also may be used and combined herein.

The use of the C-scan images 190 in the radar-like view 210 requires only a two-dimensional display of the scan data. As such, less memory and computational power may be required as compared to displaying three-dimensional data. Using the location of the beam cursor 200, one may switch to the S-scan image 220 for further detail according to the position of the beam cursor 200. The non-destructive testing system 100 described herein thus provides three-dimensional data without requiring the power and other resources to display such. The ultrasonic testing probe 110 and the non-destructing testing system 100 described herein thus may be implemented as the hand held device 140.

Figure 6:
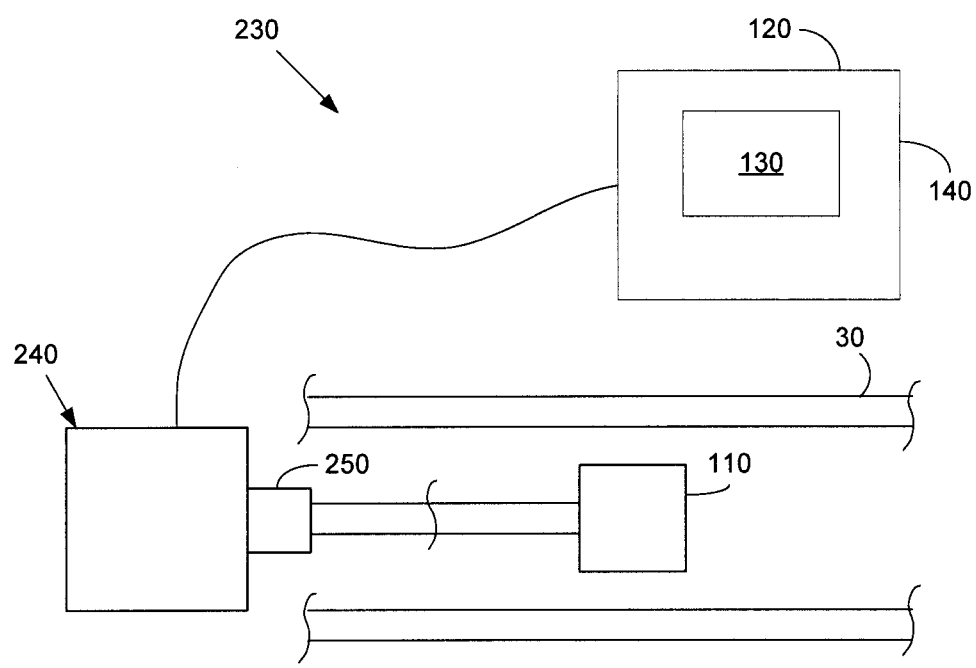
FIG. 6 is a schematic diagram of an alternative embodiment of a non-destructive testing system with an ultrasonic probe as may be described herein.

FIG. 6 shows a further example of a non-destructive testing system 230 as may be described herein. In this example, the ultrasonic probe 110 may be physically rotated. Specifically, the ultrasonic probe 110 may be attached to and rotated by a motor 240. The motor 240 may be any type of device capable of producing rotational movement. The rotational position of the ultrasonic probe 110 may be determined by a position encoder 250 and the like. Other types of positioning and drive means may be used herein. The non-destructive testing system 230 may then produce the scan images in a manner similar to that described above. Other components and other configurations may be used herein.

It should be apparent that the foregoing relates only to certain embodiments of the present application and the resultant patent. Numerous changes and modifications may be made herein by one of ordinary skill in the art without departing from the general spirit and scope of the invention as defined by the following claims and the equivalents thereof.

We claim:

1. A non-destructive testing system for testing a work piece from within the work piece, the non-destructive testing system comprising:
    an ultrasonic probe outputting at least one beam from a location within the work piece being tested;
    a control unit for controlling the ultrasonic probe;
    means for causing the beam to proceed in 360° of directionality within the work piece being tested;
    wherein the ultrasonic probe and the control unit configured obtain C-scan images and corresponding S-scan images, the C-scan images and the corresponding S-scan images are of the same portion of the work piece being tested; and
    a hand-held display in communication with the ultrasonic probe;
    wherein the hand-held display is configured to display C-scan images or corresponding S-scan images.

2. The non-destructive testing system of claim 1, wherein the ultrasonic probe comprises a two-dimensional array probe.

3. The non-destructive testing system of claim 1, wherein the ultrasonic probe comprises a translational device.

4. The non-destructive testing system of claim 1, wherein the hand-held display is configured to display the C-scan images in a radar-like view with a beam cursor.

5. The non-destructive testing system of claim 4, wherein a position of the beam cursor corresponds to a related S-scan image.

6. The non-destructive testing system of claim 1, wherein the ultrasonic probe produces a plurality of C-scan images.

7. The non-destructive testing system of claim 1, wherein the ultrasonic probe produces a plurality of S-scan images.

8. The non-destructive testing system of claim 1, further comprising a motor for rotating the ultrasonic probe.

9. The non-destructive testing system of claim 8, wherein the motor comprises a position encoder in communication with the ultrasonic probe.

10. A method of viewing non-destructive test data in connection with testing a work piece from within the work piece, the method comprising:
    maneuvering an ultrasonic probe within the work piece being tested and outputting at least one beam from a location within the work piece being tested;
    ultrasonically scanning the work piece by causing the beam to proceed in 360° of directionality within the work piece being tested;
    obtain C-scan images and corresponding S-scan images, the C-scan images and the corresponding S-scan images are of the same portion of the work piece being tested;
    displaying a plurality of C-scan images on a hand-held display;
    selecting one of the plurality of C-scan images; and
    displaying an S-scan image corresponding to the selected C-scan image on the hand-held display.

11. The method of viewing of claim 10, wherein the step of displaying the plurality of C-scan images comprises displaying the plurality of C-scan images in a radar-like view.

12. The method of viewing of claim 11, wherein the radar-like view comprises rotating a beam cursor.

13. The method of viewing of claim 12, wherein a position of the beam cursor comprises the S-scan image corresponding to the selected C-scan image.

14. The method of viewing of claim 10, wherein the displaying steps comprise displaying the scans on a hand-held device.

15. The method of viewing of claim 10, further comprising the step of resuming display of the plurality of C-scan images.

16. The method of claim 10, wherein the step of maneuvering the ultrasonic probe comprises encoding a position of the ultrasonic probe.

17. A non-destructive testing system for testing a work piece from within the work piece, the non-destructive testing system comprising:
   an ultrasonic probe outputting at least one beam from a location within the work piece being tested;
   wherein the ultrasonic probed comprises a two-dimensional array;
   a control unit for controlling the ultrasonic probe;
   means for causing the beam to proceed in 360° of directionality within the work piece being tested;
   wherein the ultrasonic probe and the control unit configured obtain C-scan images and corresponding S-scan images, the C-scan images and the corresponding S-scan images are of the same portion of the work piece being tested; and
   a hand-held display in communication with the ultrasonic probe;
   wherein the hand-held display is configured to display a plurality of C-scan images in a radar-like view or a corresponding S-scan image.

18. The non-destructive testing system of claim 17, wherein the radar-like view comprises a beam cursor.

19. The non-destructive testing system of claim 18, wherein a position of the beam cursor corresponds to a related S-scan image.

20. The non-destructive testing system of claim 17, further comprising a motor to rotate the ultrasonic probe and wherein the motor comprises a position encoder in communication with the ultrasonic probe.

* * * * *